United States Patent [19]

Novack

[11] Patent Number: 4,922,919
[45] Date of Patent: May 8, 1990

[54] METHOD FOR MEASURING OCULAR OXIDATIVE METABOLISM

[75] Inventor: Roger L. Novack, Durham, N.C.

[73] Assignee: Duke University, Durham, N.C.

[21] Appl. No.: 171,831

[22] Filed: Mar. 22, 1988

[51] Int. Cl.$^5$ .............................................. A61B 6/00
[52] U.S. Cl. .................................. 128/633; 128/665; 128/745
[58] Field of Search .............................. 128/632–634, 128/664–666, 745

[56] References Cited

U.S. PATENT DOCUMENTS

| | | |
|---|---|---|
| 3,068,742 | 12/1962 | Hicks, Jr. et al. |
| 3,123,066 | 3/1964 | Brumley |
| 3,136,310 | 6/1964 | Meltzer |
| 3,811,777 | 5/1974 | Chance |
| 3,825,342 | 7/1984 | Lubbers et al. |
| 4,223,680 | 9/1980 | Jobsis |
| 4,321,930 | 3/1982 | Jobsis et al. |
| 4,380,240 | 4/1983 | Jobsis et al. |
| 4,412,543 | 11/1983 | Vassiliadis et al. |
| 4,485,820 | 12/1984 | Flower |
| 4,569,354 | 2/1986 | Shapiro |
| 4,597,392 | 7/1986 | Opitz et al. |

OTHER PUBLICATIONS

Kreisman et al., "Local Tissue Oxygen Tension–Cytochrome a, a3 Redox Relationships in Rat Cerebral Cortex in Vivo", *Brain Research*, 218 (1981), pp. 161–174.
Duckrow et al., "Sensitive and Inexpensive Dual-Wavelength Reflection Spectrophotometry Using Interference Filters", *Analytical Biochemistry*, 125, 13–23 (1982).
Ji et al., "Micro-Light Guides: A New Method for Measuring Tissue Fluorescence and Reflectance", American Physiological Soc., (1979).
Mendelson et al., "Spectrophotometric Investigation of Pulsatile Blood Flow for Transcutaneous Reflectance Oximetry", Chem. Abstracts, (1983), pp. 93–102.

*Primary Examiner*—Kyle L. Howell
*Assistant Examiner*—John C. Hanley
*Attorney, Agent, or Firm*—Cushman, Darby & Cushman

[57] ABSTRACT

A method of measuring the oxidative metabolism of ocular tissue. The ocular tissue is alternately illuminated, with light of a sample wavelength corresponding to the absorption peak of cytochrome a,a3 and light of a reference slightly above or below the sample wavelength. Light reflected by the ocular tissue is detected and an electronic signal corresponding to said light produced. The signal corresponding to the reference wavelength is subtracted from the produced signal. In a preferred embodiment an optical probe with a first probe to deliver light to the ocular tissue and a second probe to deliver reflected light to a detector is provided. The optical probe is placed on the ocular tissue under study.

14 Claims, 3 Drawing Sheets

METHOD FOR MEASURING OCULAR OXIDATIVE METABOLISM

BACKGROUND OF THE INVENTION

The present invention relates to a method for measuring ocular metabolism and more particularly a method for measuring ocular oxidative metabolism using reflectance spectrophotometry.

Because the tissues in the interior of the eye are readily visible, conventional methods to detect diseases of the eye such as glaucoma, retinitis pigmentosa, ocular vascular occlusions or ocular tumors have been based on direct observation of the eye, direct or indirect measurements of functions such as visual acuity, electroretinography or visual evoked responses, or more invasive techniques such as tissue biopsy. Direct observation can only determine whether there are any anatomical structural changes. But the eye may appear to be normal and have oxygen related metabolic abnormalities which may lead to significant loss of function, such as is the case with diseases such as impending arterial occlusion and early glaucoma. Ocular tissue however, has not been heretofore subjected to metabolic monitoring as a predictor of ocular disease.

Reflectance spectrophotometry has been used to measure the presence of cytochrome c oxidase (hereinafter "cytochrome $a,a_3$") such as is disclosed in Duckrow et al., Analytical Biochemistry 125:13-23, 1982. In the Duckrow method a reference and sample light beam having two separate wavelengths illuminates a tissue alternately. In Duckrow the tissue illuminated is the cerebral cortex of a rat. The light reflected by the tissue is detected and converted to an electronic signal and the signal associated with the reference wavelength is separated therefrom. However, this method is limited to the tissue region from which the externally applied light can penetrate and reflect to the detector. In addition, the optical signals that are derived are from relatively large areas of tissues rather than from small areas as would be desirable in the eye. Further, these methods have not been used in the eye because in order to optically detect cytochrome $a,a_3$ through the front of the eye, measurements must take into account optical and metabolic contributions of photopigments, melanin, the cornea, and the lens.

Micro-light guides have been used in methods for measuring tissue fluorescence and reflectance of small areas of tissue as disclosed in Ji et al., American Journal Physiology, 236(3): C 144-156, 1979. This reference discloses use of this method in relation to rat liver and contains no discussion on its use in the eye.

SUMMARY OF THE INVENTION

It is an object of the present invention to measure ocular tissue metabolism.

It is still another object of the present invention to measure ocular tissue metabolism while cancelling the metabolic contributions of melanin and photopigments.

It is yet another object of the present invention to bypass ocular tissue at the front of the eye and measure the metabolism of ocular tissue at the back of the eye.

It is a feature of the present invention that an optic probe is inserted into the eye, thereby allowing small areas to be illuminated and other tissue not under study to be bypassed.

It is a feature of the present invention that optic nerve and retinal metabolism may be measured noninvasively through the front of the eye.

It is an advantage of the present invention that early detection of eye disease, such as glaucoma and retinitis pigmentosa, can be made.

BRIEF DESCRIPTION OF THE DRAWINGS

FIG. 4 is a block diagram of a fourth apparatus used in the present invention.

FIG. 5 is a block diagram of a fifth apparatus used in the present invention.

DETAILED DESCRIPTION OF THE PREFERRED EMBODIMENTS

The present invention is a method for measuring the oxidative metabolism of ocular tissue by measuring the reduction to oxidation ratio of concentrations of cytochrome $a,a_3$ in intact tissue. Cytochrome a, $a_3$ is the terminal member of the respiratory chain and reacts directly with molecular oxygen. Because cytochrome $a,a_3$ relates to oxidative metabolism of ocular tissue, the measurement of cytochrome $a,a_3$ permits the early detection of diseases due to changes in oxidative metabolism prior to actual anatomical damage. This early detection leads to early treatment and the prevention of loss of vision.

Figure 1:
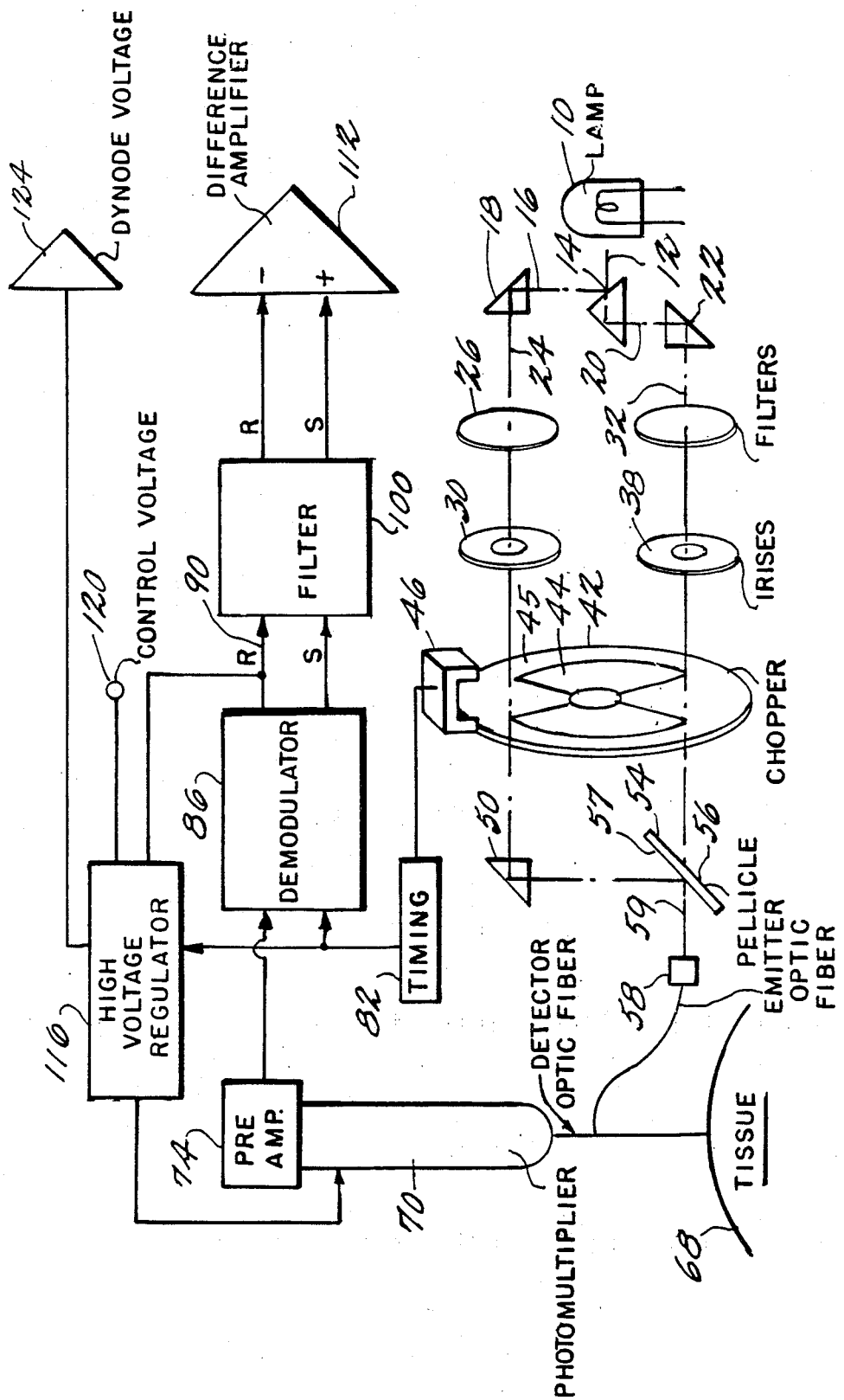
FIG. 1 is a block diagram of a first apparatus used in the present invention.

As depicted in FIG. 1, a light beam 12 is generated by a light source. In the embodiment shown in FIG. 1, the light source 10 is a lamp preferably a tungsten halogen lamp. However, light source 10 may be any light source which can generate light of wavelengths of 605, 590, and 620 nm respectively. For instance, this light source 10 lamp may also be a laser diode or some other laser source. The light source 10 can also be a pair of lasers one generating light at a reference wavelength and the other generating light at a sample wavelength, each laser pulsating so that the tissue 68 receives light at the reference and sample wavelength alternately. The light beam 12 is divided into two components 16 and 20 respectively which travel along parallel paths. First component 16 is transmitted to a prism or mirror 18 and then on to a monochromatic filter 26 along light path 24. Light of all wavelengths, except for 605 nm is filtered out by filter 26. The wavelength 605 nm is chosen because it is a maximum absorption peak of cytochrome $a,a_3$. Filter 26 can be replaced by a variable monochromator or any other structure which filters the wavelength of light. The intensity of the light is then adjusted by an iris diaphragm 30 or any other suitable structure.

The second component 20 of light beam 12 is transmitted to a prism 22 and then along a light path 32 to a filter 34. Filter 34 filters out all wavelengths of light other than 590. The 590 nm wavelength can be replaced with a 620 nm wavelength. The 590 and 620 nm are reference wavelengths and are chosen because these wavelengths are near but not on the cytochrome $a,a_3$ absorption peak and because its contribution to the absorption at 590 or 620 nm varies in the same manner as that of 605 nm when blood volume and hemoglobin oxygen saturation are altered.

Since absorption at the sample wavelength is altered not only by absorption of cytochrome a,$a_3$ but also by light scattering, changes in blood volume and hemoglobin saturation, a wavelength for reference was selected which undergoes an equal optical density change as that of 605 nm when light scattering or blood volume is altered and when there are shifts in the Hb/HbO$_2$ ratio.

The intensity of component 20 is adjusted by iris diaphragm 38. Irises 30 and 38 adjust the intensity of components 16 and 20 so that the intensities are the same.

The optical paths 24 and 32 of components 16 and 20 are parallel to the axis 44 of a motor driven chopper blade 42. The chopper blade 42 has apertures 44 and solid sections 45 and produces chopper interruption of one light path at a time. The chopper blade 42 is spun at a preset rate, typically 1800 rpms, thereby producing illumination to prism or mirror 50 and pellicle 54 alternatively. The chopper blade 42 may be replaced by any other structure which interrupts each light path alternately at a preset rate.

Component 16 strikes a surface 57 of pellicle 54 and is deflected and component 20 strikes a surface 56 of pellicle 54 and is transmitted. Components 16 and 20 are then added to form light beam 60. Pellicle 54 passes light at the sample wavelength and reflects light at the reference wavelength.

Figure 2:
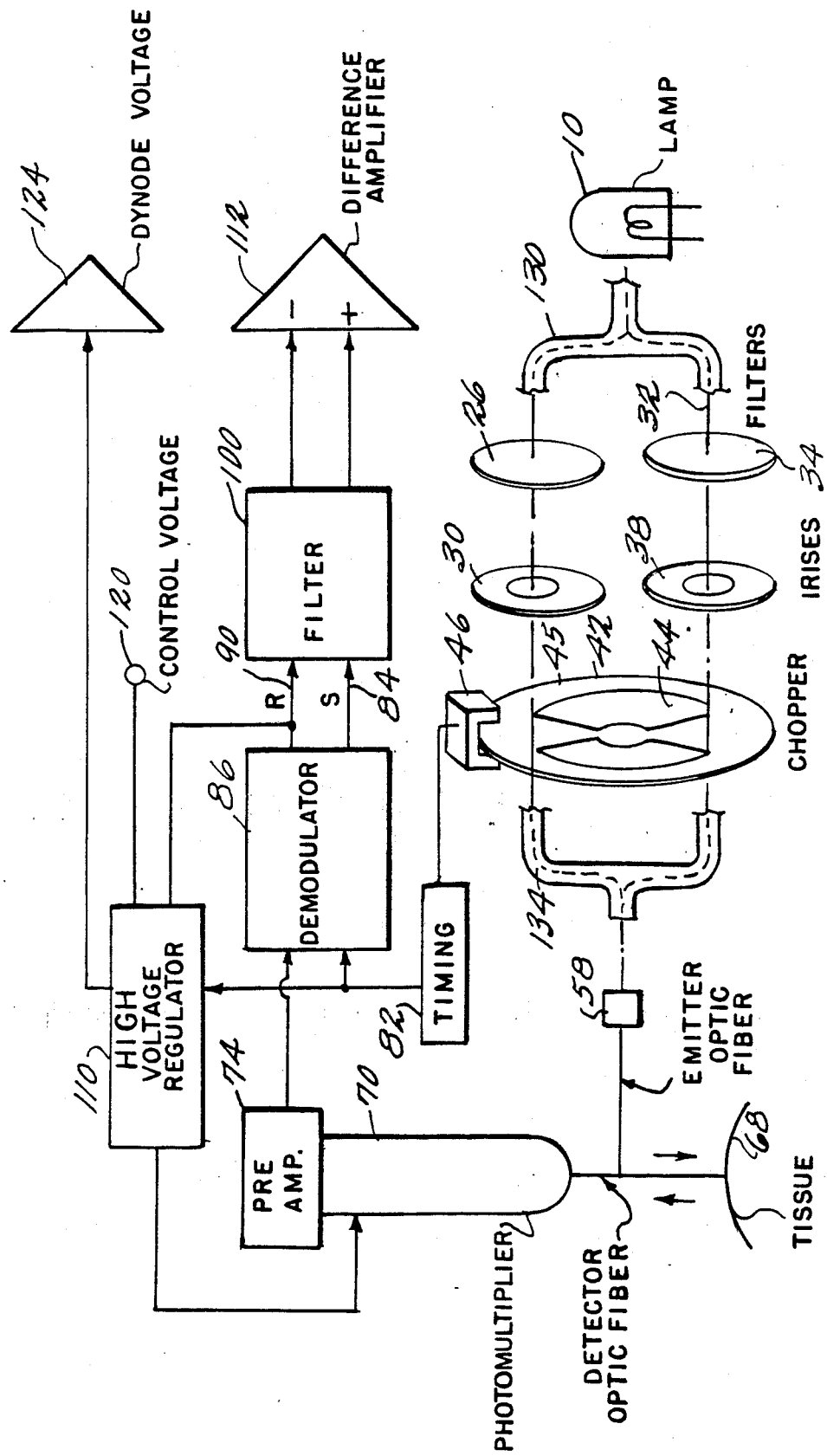
FIG. 2 is a block diagram of a second apparatus used in the present invention.

Alternatively, filters 25 and 34 (and additional filters, if necessary) may be placed on a wheel 40 as in FIG. 2. This would allow a single light path 17 from lamp 10 to pass through the rapidly alternating monochromatic filters on the filter wheel 40. The photodiode interrupter module 46 on the filter wheel 40 can be used to provide indicator pulses to the timing circuitry as in FIG. 1. This technique eliminates the requirements for a dual light path 24 and 32, prisms or mirrors 18, 22, and 50, irises 30 and 38, and pellicle 54 with attendant hardware. In addition, more than two filters can be placed on the wheel to allow, for example, simultaneous measurements of cytochrome a, $a_3$ reduction/oxidation state and hemoglobin disoxygenation/oxygenation state (i.e. oximetry).

As seen in FIG. 1, a connector 58 couples the light traveling along light path 59 via an air gap and optical lenses (not shown) inside connector 58 to an optical probe 62.

Optical probe 62 comprises an emitter fiber optic 64 and a detector fiber optic 66 glued together in a double barrelled arrangement. These fiber optics are microfibers having a preferred diameter of 20–50 μm. Each of these fibers 64 and 66 is coated with a glass material which has a lower index of refraction than the core of each fiber 64 and 66. This permits total internal reflection of the light passing through the core. Since ambient light can pass through the coating and interface with biological signals, the fibers 64 and 66 are coated with black insulating tubing except for sections where the fibers 64, 66 enter tissue 68. In these areas, the fibers 64 and 66 are either covered with black paint, sputter coated with gold or encased in a stainless steel sheath. The fibers 64 and 66 are held in place by the sheath casing with an internal insulation material or an adhesive such as cyoanoacrylate. While an optical probe 62 is disclosed, the method of the present invention covers any means of delivering light at a reference and sample wavelength to the interior of the eye.

Light scattered back from tissue 68 travels through detector fiber 66 and is detected by photomultiplier 70. Optical probe 62 is typically placed within a millimeter of tissue 68. The placement of the detector fiber 66 so near tissue being scanned eliminates specular reflection complications. The photomultiplier tube 70 is exposed to light returning from tissue 68 illuminated alternately at sample and reference wavelengths and converts said light to sample and reference voltage signals.

A photo diode interrupter module 46 is placed on the light chopper 42. This photo diode interrupter module 46 provides a syncronizing pulse related to the rate of revolution of light chopper 42 to a timing circuit 82. The timing circuit 82 produces trigger pulses and supplies these pulses to demodulator 86 which demodulates the reference and sample signal so that the photomultiplier tube 70 output is split into two continuous signals representing the intensity of light returning from the tissue at each wavelength. Noise in the sample and reference signal is filtered by electronic filters 100 to typically provide a maximum resolution of 0.8 millivolts difference between sample and reference signals with a minimum time constant of one second. The reference signal is then subtracted from the sample signal by a difference amplifier 112. This output signal may be displayed on a chart recorder or the output may be interfaced with a computerized data processing system.

The signal generated by the photomultiplier tube 70 is amplified by preamp 74. The gain of photomultiplier tube 70 is controlled by a high voltage regulator 116. High voltage regulator 116 compares the reference signal to an adjustable control voltage 120. In addition, feedback induced variations in the reference signal are recorded to provide continuous monitoring of the amount of hemoglobin in the optical field since vascular changes are the main source of optical density shifts. Because of this feedback control, and because the photomultiplier tube 70 responds logarithmically to dynode voltage 124 shifts, changes in the photomultiplier voltage supply are directly related to logarithmic optical density changes and hemoglobin concentration thereby eliminating the error that may occur due to these factors.

The apparatus is calibrated by setting system output to 0 when no light is directed to tissue 68. The tissue 68 is then presented with light at the reference wavelength only and the intensity of the reference illumination is adjusted to obtain full scale pin deflection within normal cathode potential and anode current of the photomultiplier tube 70. Then, light at a sample wavelength is presented to the tissue alternately with the reference light and sample light intensity is adjusted to equal reference intensity. Subsequently, differences between sample and reference light intensity are recorded as percentages of the full scale illumination signal level. The voltage applied to the photomultiplier 70 is used as an index of the relative local blood volume and is expressed in volts or percent changes by the dynode voltage applied to obtain the initial reference illumination signal.

The measurement of cytochrome a,$a_3$ reduction/oxidation in the eye is problematic because in order to detect cytochrome a,$a_3$ through the front of the eye, the measurement must take into account the metabolic contributions of the cornea, the lens, melanin, and photopigments. In order to ensure, for example, that the metabolism of the retina or optic nerve in the interior of the eye is selectively detected, the optical probe 62 must bypass the cornea and the lens to the retina or optic nerve to be examined. Alternatively, the optic nerve or retina can be observed through the cornea and the lens and the data obtained compared with data obtained by the probe 62 when the probe 62 bypasses the cornea and lens thereby determining the metabolic contribution of the retina or optic nerve. At this point optical probe 62 need not be used. The method of the present invention can also selectively measure metabolic changes of any tissue in the optical pathways, such as the cornea, the lens or the optic nerve or retina by changing, via focusing optics such as a lens, the intensity of light beam 60 which illuminates the tissue 68. For example, a larger and more focused beam can detect retina and optic nerve by overwhelming small amounts of absorption which occur in the cornea or lens. A less bright and more diffuse beam will not reach the posterior structures and can be used to detect cornea lens metabolic changes.

A correction for the absorption of cytochrome $a,a_3$ by other components of the eye, such as melanin and photopigments must be performed. These absorbers of light of the cytochrome $a,a_3$ peak wavelength occur uniquely in the eye because of the function of the eye in detecting light.

To correct for absorption by photopigments, a bright flash timed to begin before the tissue is illuminated with light beams 16 and 20 is performed. This bright flash is a flash of light that may be produced by lamp 10 or any other light source capable of producing white light, such as a strobe light. This effectively bleaches the photopigments and changes their absorption characteristics so that they do not absorb light in the wavelength studied.

The melanin layer is a relatively homogeneous layer adjacent to the retina. The absorption characteristics of the melanin layer are very slow to change with time, but the absorption of light by melanin is greater with shorter wavelengths. Therefore, the melanin can act as a screen to activity of cytochrome $a,a_3$ posterior to it and allow the detection of cytochrome $a,a_3$ in the retina, for example. This enables a pure detection of retinal metabolic function without interference from other tissues, such as the retinal pigment epithelium.

To correct for melanin absorption in the eye, the absorption characteristics of retina at the chosen wavelength are compared with the same wavelength characteristics of optic nerve, over which there is no melanin. This enables an approximate measurement of the melanin light absorption component for each wavelength. If this melanin component is different for the two wavelengths, the difference is then added to the light of higher wavelength or subtracted from the light of lower wavelength to ensure equal sample and reference wavelength light levels.

Figure 3:
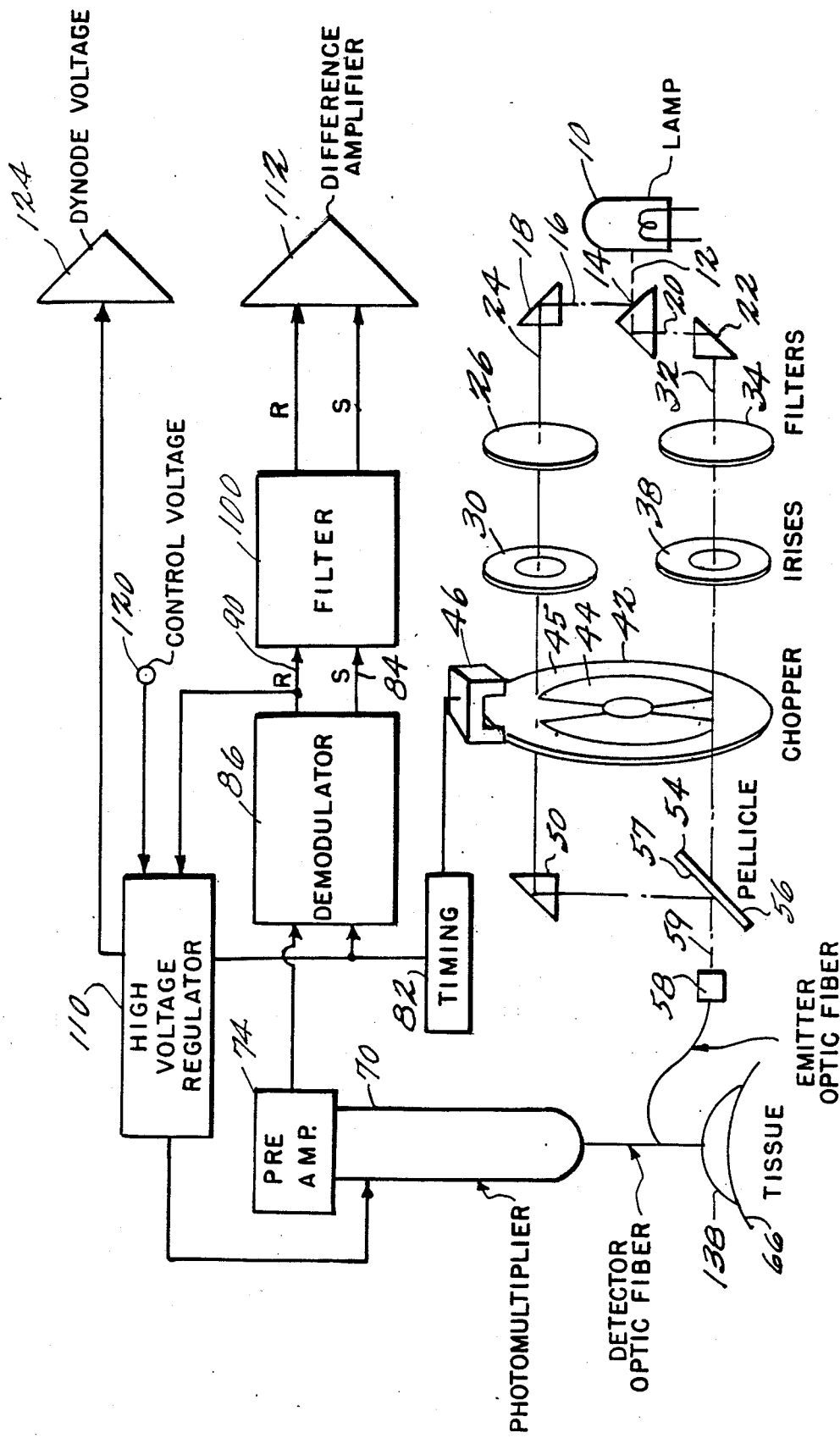
FIG. 3 is a block diagram of a third apparatus used in the present invention.

FIG. 3 depicts another apparatus used in the method of the present invention in which prisms 18, 20 and 22 are replaced by Y-shaped optical bundle 130 and prisms 50 and pellicle 54 are replaced by Y-shaped optical fibers bundle 134.

FIG. 4 depicts yet another apparatus used in the method of the present invention in which a contact lens 138 is placed on corneal tissue 68 and probe 62 is secured on contact lens 138. An optical coupling jelly may be placed between the lens 138 and the tissue 68. This optical coupling jelly has a refractive index different from air so that the refractive errors resulting from air may be minimized.

FIG. 5 depicts another apparatus used in the method of the present invention in which the optical probe 62 is placed in front of the contact lens 138 with a plurality of lenses (not shown) disposed inside beam adjuster 61 therebetween. The diameter may be adjusted with irises or any other defocusing mechanism also disposed in beam adjuster 61. Alternatively, first optical fiber 64 may be eliminated and the light directed to the contact lens 138.

The method of the present invention can also measure the saturation of oxygenated and disoxygenated hemoglobin by changing the reference wavelengths. wavelengths.

While the present invention has been described in connection with what is presently considered to be the most practical and preferred embodiments, it is to be understood that the invention is not limited to the disclosed embodiment, on the contrary, it is intended to cover various modifications in equivalent methods included within the spirit and scope of the appended claims. Therefore, persons of ordinary skill in the field are to understand that all such equivalent methods are to be included within the scope of the following claims.

What is claimed is:

1. A method to detect oxidative metabolism of ocular tissue comprising the steps of:
   bleaching photopigments in said ocular tissue with a bright flash;
   generating a first beam of optical energy of a predetermined reference wavelength;
   generating a second beam of optical energy of a predetermined sample wavelength;
   alternately illuminating said ocular tissue with said first beam and said second beam;
   detecting optical energy reflected by said ocular tissue;
   converting said optical energy to a first electronic signal;
   subtracting a second electronic signal from said first electronic signal to obtain a third electronic signal; and
   processing said third electronic signal to determine said oxidative metabolism.

2. A method as in claim 1 wherein said illuminating step includes transmitting said first and second beam through a first optical fiber.

3. A method as in claim 2 wherein said detecting means comprises the step of transmitting said reflected light through a second optical fiber to a detector.

4. A method as in claim 3 further comprising the step of placing said first and second optical fiber on said ocular tissue.

5. A method as in claim 4 further comprising the steps of converting said detected optical energy to an electronic signal comprised of a signal corresponding to said reference wavelength and a signal corresponding to said sample wavelength and subtracting the signal corresponding to said reference wavelength from said electronic signal associated with said sample wavelength.

6. A method of measuring the presence of cytochrome $a, a_3$ in ocular tissue comprising the steps of:
   bleaching photopigments in said ocular tissue with a bright flash;
   generating a source beam of light of a predetermined intensity;
   dividing and filtering said source beam into a first component of a first predetermined wavelength and a second component of a second predetermined wavelength;

alternately transmitting said first and second components to a first optical fiber;

transmitting light reflected from said ocular tissue to a photomultiplier tube;

converting said reflected light to an electronic signal;

subtracting a signal associated with said first wavelength from a signal associated with said second wavelength;

processing said signal associated with said second wavelength to determine the concentration of said cytochrome a, $a_3$.

7. A method as in claim 6 further comprising the step of adjusting the intensity of said beam so that said beam reaches the posterior of the eye.

8. A method of measuring the oxygen metabolism of ocular tissue comprising the steps of:

bleaching photopigments in the ocular tissue with a bright flash;

placing a contact lens on the cornea of the eye;

generating a first beam of light at a first predetermined wavelength;

generating a second beam of light at a second predetermined wavelength;

transmitting said first and second beam of light through said contact lens to ocular tissue;

detecting the light reflected by said ocular tissue;

converting said reflected light to an electronic signal;

subtracting an electronic signal associated with said first wavelength from the electronic signal associated with said second wavelength thereby forming a resultant electronic signal; and processing said resultant electronic signal to determine the oxygen metabolism of the ocular tissue.

9. A method as in claim 8 further comprising the steps of converting said reflected light to an electronic signal and subtracting a signal associated with said first predetermined wavelength from said electronic signal.

10. A method as in claim 9 further comprising the step of transmitting a bright flash through said contact lens to said ocular tissue prior to said first generating step.

11. A method as in claim 10 further comprising the step of correcting said reflected signal for a melanin component.

12. A method of detecting optic nerve and retinal metabolism comprising the steps of:

bleaching photopigments in said ocular tissue;

generating a source light beam;

splitting said source beam into a first component and a second component;

filtering said first component to exclude all wavelengths except a predetermined first wavelength;

filtering said second component to exclude all wavelengths except a predetermined second wavelength;

placing an optic probe having a first optical fiber and a second optical fiber therein near the optic nerve;

transmitting said first component and said second component alternatively through said first optical fiber;

transmitting light reflected by said optic nerve through the second optical fiber to a detector; and converting said reflected light to a first electronic signal; and subtracting a second electronic signal from said first electronic signal to obtain a third electronic signal;

processing said third electronic signal to obtain said ocular metabolism.

13. A method as in claim 12 further comprising the step of subtracting a signal associated with said first predetermined wavelength from a signal associated with said second predetermined wavelength.

14. A method as in claim 13 further comprising the step of passing a bright flash of light through said first optical fiber prior to alternatively transmitting said first and second components.

* * * * *